United States Patent [19]

Zaromb et al.

[11] Patent Number: 4,591,414
[45] Date of Patent: May 27, 1986

[54] METHOD OF DETERMINING METHANE AND ELECTROCHEMICAL SENSOR THEREFOR

[75] Inventors: Solomon Zaromb, Hinsdale; Takaaki Otagawa, Westmont; Joseph R. Stetter, Naperville, all of Ill.

[73] Assignee: The United States of America as represented by the United States Department of Energy, Washington, D.C.

[21] Appl. No.: 644,467

[22] Filed: Aug. 27, 1984

[51] Int. Cl.⁴ .................... G01N 27/28; G01N 27/52
[52] U.S. Cl. .................... 204/1 T; 204/406; 204/412; 204/415; 204/431; 204/432
[58] Field of Search ........... 204/431, 432, 411, 412, 204/1 K, 415, 406

[56] References Cited

U.S. PATENT DOCUMENTS

| | | | |
|---|---|---|---|
| 751,897 | 2/1904 | Bodländer | 204/431 X |
| 2,862,859 | 12/1958 | Grosskopf | 204/1 T |
| 3,305,457 | 2/1967 | Hyman | 204/1 T |
| 3,342,558 | 9/1967 | Reinecke | 436/30 |
| 3,408,269 | 10/1968 | Hersch | 204/1 T |
| 3,701,632 | 10/1972 | Lovelock | 436/151 |
| 3,776,832 | 12/1973 | Oswin et al. | 204/411 |
| 3,824,168 | 7/1974 | Oswin et al. | 204/411 |
| 3,836,449 | 9/1974 | Lovelock | 204/277 |
| 3,909,386 | 9/1975 | Oswin et al. | 204/408 |
| 4,169,779 | 10/1979 | Tataria et al. | 204/415 X |
| 4,184,937 | 1/1980 | Tataria et al. | 204/1 T X |
| 4,227,984 | 10/1980 | Dempsey et al. | 204/408 |
| 4,329,214 | 5/1982 | Spritzer et al. | 204/431 |
| 4,406,770 | 9/1983 | Chan et al. | 204/432 X |
| 4,522,690 | 6/1985 | Venkatasetty | 204/1 T |

FOREIGN PATENT DOCUMENTS 10036 10/1970 Japan ................................ 204/431

OTHER PUBLICATIONS

G. Muto et al., Analysis and Instrument, vol. 6, No. 5, pp. 287–291, (1968).
Victor H. Regener, "Automatic Ozone Recorder-Small Model", Univ. New Mexico, pp. 1, 2, (1956).

Primary Examiner—G. L. Kaplan
Attorney, Agent, or Firm—William Lohff; Hugh W. Glenn; Judson R. Hightower

[57] ABSTRACT

A method and instrument including an electrochemical cell for the detection and measurement of methane in a gas by the oxidation of methane electrochemically at a working electrode in a nonaqueous electrolyte at a voltage about about 1.4 volts versus R.H.E. (the reversible hydrogen electrode potential in the same electrolyte), and the measurement of the electrical signal resulting from the electrochemical oxidation.

19 Claims, 10 Drawing Figures

METHOD OF DETERMINING METHANE AND ELECTROCHEMICAL SENSOR THEREFOR

CONTRACTUAL ORIGIN OF INVENTION

The U.S. Government has rights in this invention pursuant to Contract No. W-31-109-ENG-38 between the U.S. Department of Energy and the University of Chicago representing Argonne National Laboratory. The U.S. Department of the Interior, Bureau of Mines, provided funds in sponsorship of the invention.

BACKGROUND OF THE INVENTION

This invention relates to methane detection and more particularly to the direct electrochemical measurement of methane concentration in a gas. Direct electrochemical measurement is intended to refer to the measurement of an electrical signal generated by a chemical reaction.

Detection and measurement of methane in mines has long been important to the mining industry. In general, present methane-detecting instruments operate by measuring changes in the resistance of a heated platinum filament caused by catalytic oxidation of a flammable gas. In copending applications Ser. No. 585,699 filed Mar. 2, 1984 entitled Sensor Array for Toxic Gas Detection and Ser. No. 585,721 filed Mar. 2, 1984 entitled Combined Sensor Device for Detecting Toxic Gases, instruments are disclosed in which a filament is used to heat a gaseous component such as methane to form oxidation products. While the power levels for these instruments using hot filaments are not necessarily excessive, they are above desired values for the detection of methane in mines. Further, a second detecting device is often required to detect the oxidation products of methane.

Accordingly, one object of the invention is an instrument for the detection of methane. A second object of the invention is an instrument for the detection of methane which operates at a low power level. A third object of the invention is an instrument which operates at a low current level. Another object of the invention is an instrument responding to methane in the absence of air. An additional object of the invention is an instrument with a sensor capable of detecting methane by electrochemical oxidation at ambient temperatures. A further object of the invention is an instrument in which the electrochemical oxidation of methane results directly in an electrical signal representative of methane. These and other objects will become apparent from the following detailed description.

SUMMARY OF THE INVENTION

Briefly, the invention is directed to a method and instrument for the detection and measurement of methane in a gas by oxidizing methane electrochemically in a nonaqueous electrolyte at a voltage above about 1.4 volts versus R.H.E. (where R.H.E. is defined as the reversible hydrogen electrode potential in the same electrolyte or the equivalent thereof) and measuring the electrical signal resulting from the electrochemical oxidation. More particularly, the method includes the steps of providing an electrochemical cell with at least two electrodes (including a working electrode) separated by a nonaqueous electrolyte, and forming an interface between the electrolyte and the working electrode, providing an oxidizing voltage of above about 1.4 volts versus R.H.E. at the working electrode, exposing the working electrode to a gaseous sample at the interface with the nonaqueous electrolyte to form methane oxidation products (in case methane is present in the sample) yielding an electrical signal representative of the concentration of those products, and measuring the signal level. The instrument includes electrochemical cell means including at least two electrodes (including a working electrode) and a nonaqueous electrolyte separating the electrodes with an interface between the electrolyte and the working electrode, means for applying an oxidizing potential above about 1.4 volts versus R.H.E. to the working electrode, means for exposing the working electrode to a gaseous sample at the interface with the nonaqueous electrolyte so that part of any methane present in said sample is electrochemically oxidized and an electrical signal is generated, and means for measuring the signal level representative of the concentration of methane.

The invention has several advantages. The instrument may be operated at low levels of power and current (i.e., less than 180 milliwatts and less than 10 milliamperes). Methane may be oxidized at low ambient temperatures. The instrument is capable of oxidizing methane at levels approaching 100% in the absence of air. In addition, direct electrochemical measurements may be obtained which are representative of the methane concentration. Also, a reference cell may be incorporated in the instrument to cancel or reduce the effects of background current variations on the signal being measured.

DETAILED DESCRIPTION OF THE PREFERRED EMBODIMENT

With electrochemical sensors, methane is not readily oxidized. At room temperature, use of common aqueous electrolytes limits the working electrode potential to slightly over 1.2 volts versus R.H.E. since water begins to decompose above that approximate potential. For the oxidation of methane, it was found necessary to increase the working electrode potential to above 1.4 volts versus R.H.E. At this potential it was found that nonaqueous electrolytes must be used to essentially avoid decomposition of the electrolyte and the formation of a reliable signal. It was further found that a special interface of wicking material between the electrode and the electrolyte improved the performance and life of the sensor.

The nonaqueous electrolyte contains a salt dissolved in a nonaqueous solvent. With solvents such as propylene carbonate or $\gamma$-butyrolactone, salts such as NaClO$_4$ or LiClO$_4$, or their mixtures, provide an electrolyte which aids in the generation of signals representative of methane. A suitable working electrolyte can be made from between 1 and 3 moles/liter of NaClO$_4$ or LiClO$_4$ in $\gamma$-butyrolactone.

Means are provided to apply a voltage to the electrode with the voltage being sufficient to cause oxidation of at least part of any methane that may diffuse from the sample to the electrode-electrolyte interface. Usually, the potential may be controlled by a potentiostat. The potential is above about 1.4 volts and preferably at least about 1.5 volts versus R.H.E.

The gas sample that is to be tested for methane may be introduced to the working electrode through an inlet tube or other suitable means for introducing the sample.

As methane is oxidized, a current signal is generated between the working electrode and the second electrode. As illustrated in FIGS. 6–9, the signal is representative of the methane in the sample.

The signal is measured by an ammeter or other suitable current-measuring means. Typically, the signal is in the order of microamperes as illustrated in FIGS. 6–9.

Figure 10:
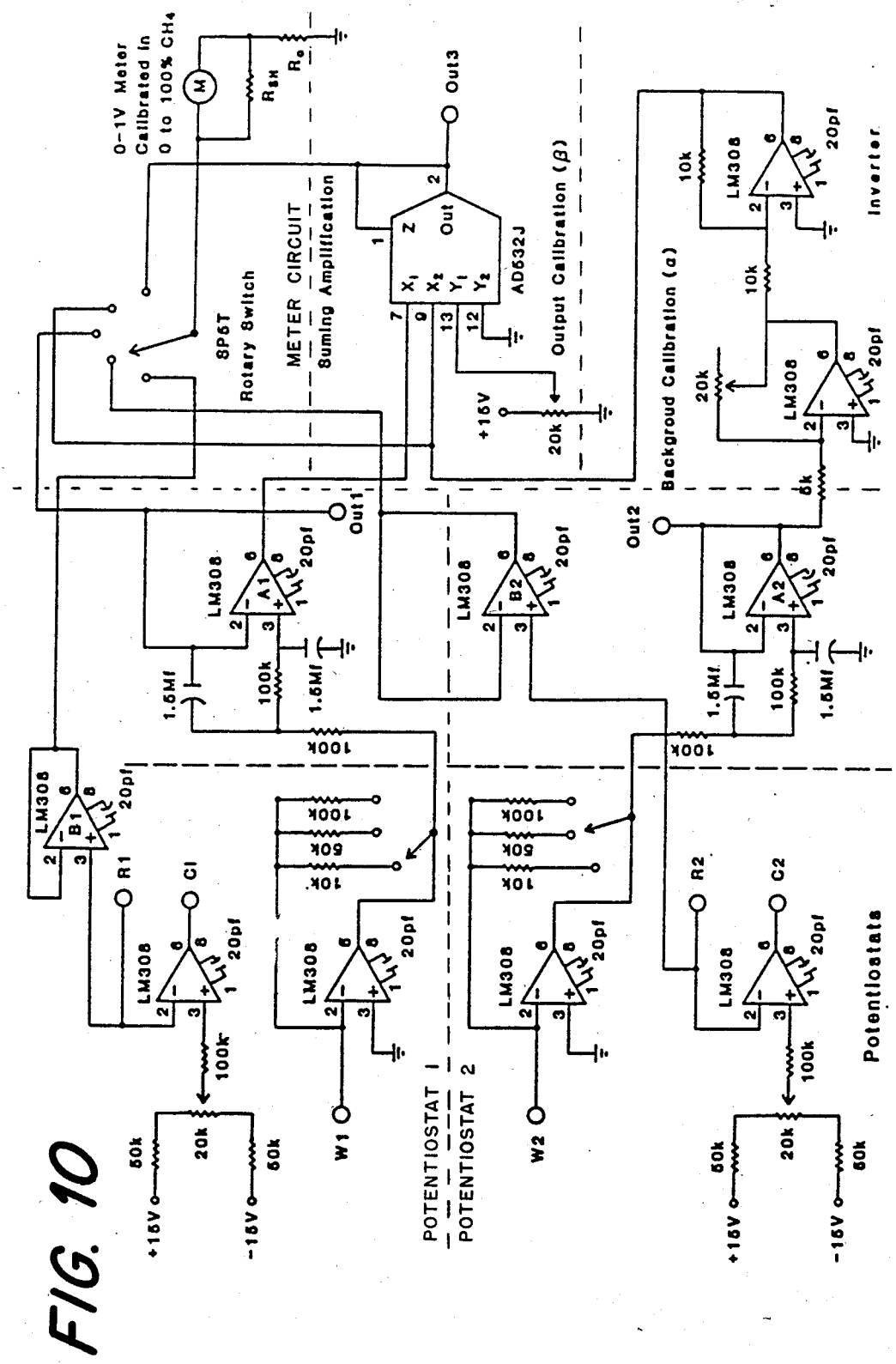
FIG. 10 is a diagram of a compensating circuit used in conjunction with the embodiment of FIG. 1.

The electrodes are constructed of a suitable catalyst on a current collector. A gas permeable membrane serves to separate the catalyst from the adjacent chamber through which the gas is introduced. Opposite the membrane is the nonaqueous electrolyte. In addition to one or two working electrodes, the instrument preferably includes a reference electrode for measuring and controlling the potential of the working electrode(s) and a counter electrode that completes an electrochemical cell reaction when an oxidizable species reaches one of the working electrodes. As illustrated in FIG. 10, the instrument further includes circuitry by which each working electrode may be separately controlled, a meter circuit, a calibration circuit, and a circuit for combining inputs to provide the net signal output.

Each electrode is preferably constructed of a platinum black catalyst and a platinized Pt-mesh current collector. Responses to methane may also be obtained with other catalysts such as a cobalt spinel having the formula Co$_3$O$_4$.

The electrode is preferably formed by depositing a catalyst bed of Pt-black powder mixed with Teflon particles in a thin porous Teflon membrane about 0.20 mm thick or less by means of filtering techniques. The Teflon concentration is above about 20 weight-% and preferably about 30–40 weight-%. The test cell was constructed of working, reference and counter electrodes, and a nonaqueous electrolyte composed of 1 M NaClO$_4$ in $\gamma$-butyrolactone.

The membrane over the electrode through which the gas permeates to the electrode is chemically inert to the electrode and nonaqueous electrolyte. Preferably, the membrane is porous, has a thickness of about 0.20 mm or less, and is formed of Teflon.

Particularly when the electrode is arranged above the electrolyte, a wick is preferably provided to insure a supply of electrolyte to maintain the interface with the working electrode. The gas sample is introduced through the membrane to the interface where oxidation occurs.

A porous Teflon (polytetrafluoroethylene) membrane serves both to support the working electrode and to confine the electrolyte near the electrode-electrolyte interface so as to permit diffusion of any methane in a gas sample to the interface. However, without the wicking arrangement, the nonaqueous electrolyte tends to permeate gradually into the membrane pores so as to gradually clog the pores and block access of gas to the electrode. The use of wicking material near the electrode helps to confine the electrolyte and prevent or reduce the clogging of the pores in the Teflon membrane.

An alternative way of minimizing the flooding problem is to use a very thin membrane of chemically inert nonporous plastic material that is insoluble in, and impervious to, the nonaqueous electrolyte, e.g., of polytetrafluoroethylene, both as a support for the electrode and a means for confining the electrolyte. Provided that the nonporous membrane is sufficiently thin (e.g., 0.01 mm or less), enough methane may diffuse therethrough to provide a measurable methane signal.

Figure 1:
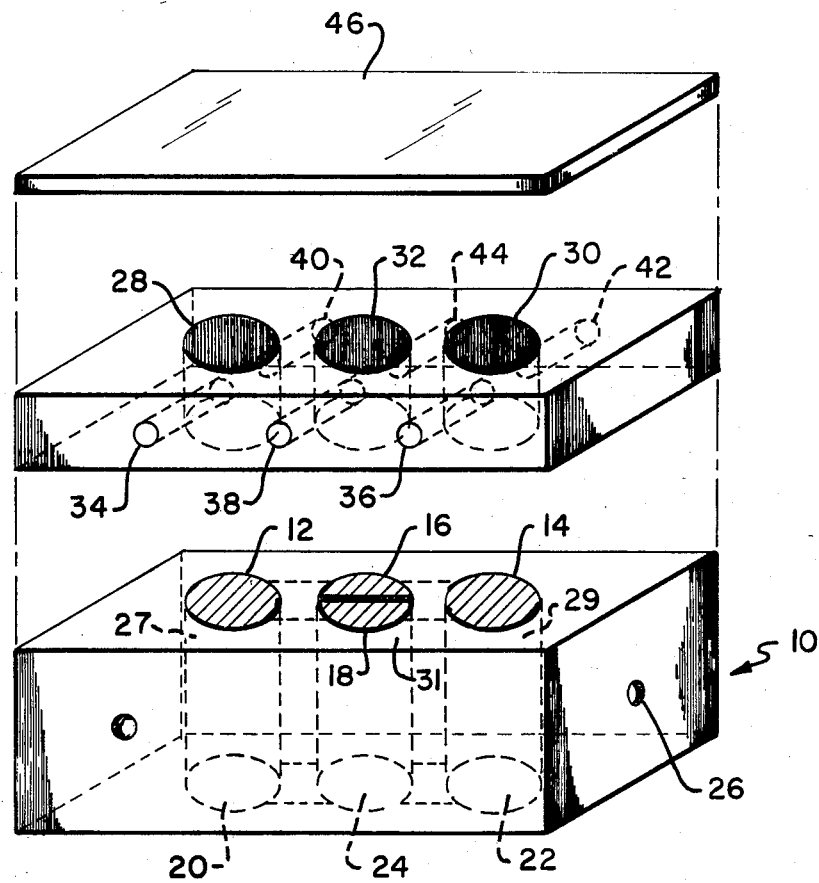
FIG. 1 is an exploded view of one embodiment of a sensor of the invention with portions separated to illustrate the electrodes.
Figure 2:
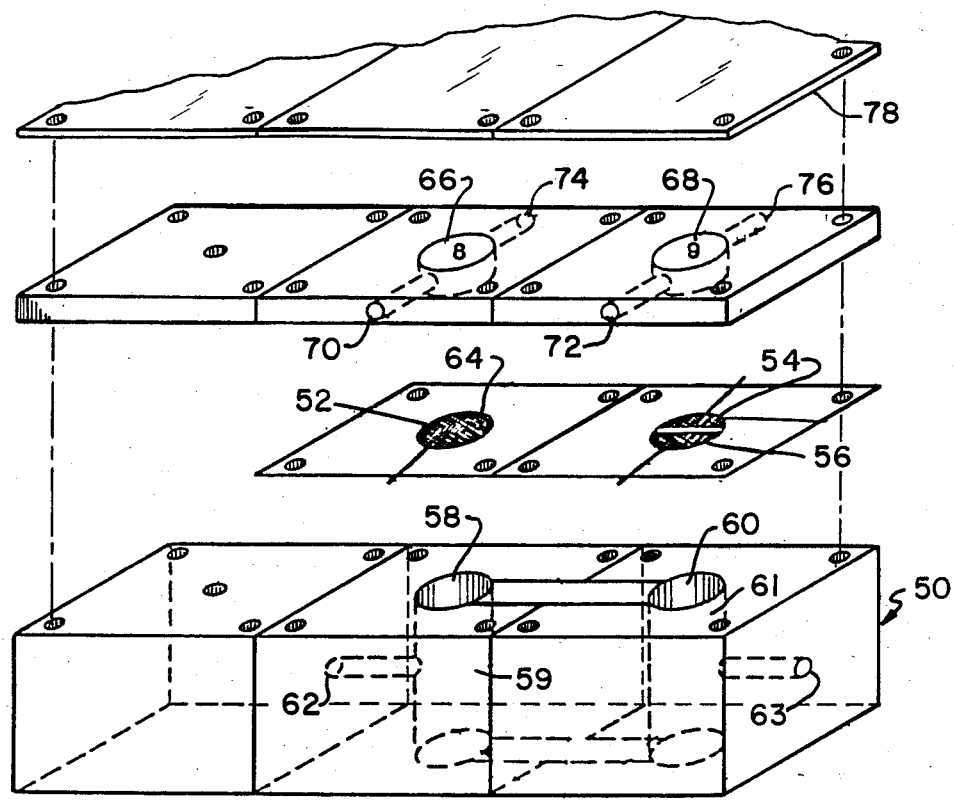
FIG. 2 is an exploded view of a second embodiment of a sensor of the invention.
Figure 3:
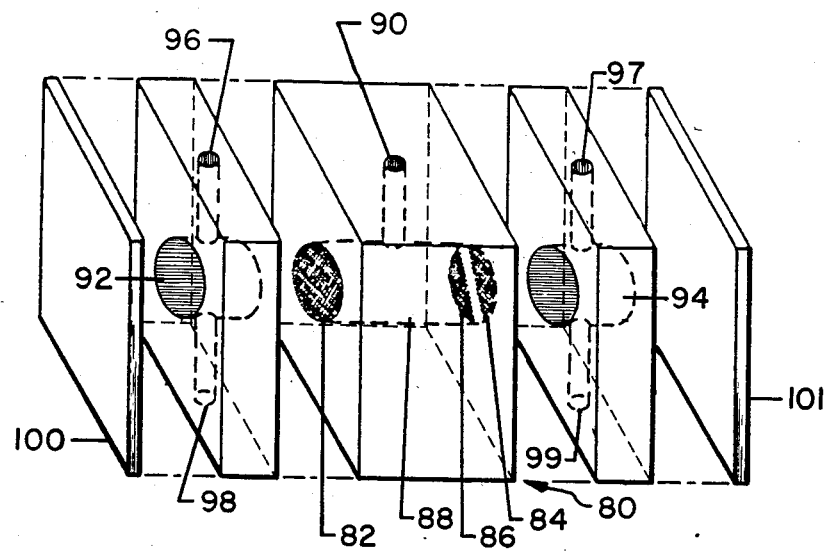
FIG. 3 is an exploded view of a third embodiment of a sensor of the invention.

Three sensors of the invention are illustrated in FIGS. 1–3. In the horizontal sensor 10 of FIG. 1, the electrode system includes working electrodes 12 and 14, counter electrode 16 and reference electrode 18 next to electrode 16. Each electrode is preferably constructed of a platinum black catalyst and a platinized Pt-mesh current collector on a Teflon membrane. Chambers 20, 22 and 24 contain nonaqueous electrolyte wicks 27, 29 and 31, respectively, in contact with the electrodes with added electrolyte being available through electrolyte inlet 26. The structure and composition of the wicks are of the type described below in the explanation of FIG. 4. Above the electrodes are chambers 28, 30 and 32 to provide contact between gas and the electrodes. Gas, viz. air, is admitted and removed via inlets 34, 36, and 38 and outlets 40, 42 and 44. Cover 46 is provided over chambers 28, 30 and 32 to insure proper flow control of the gas through the chambers. Alternatively, if the sensor is to operate in the diffusion mode, i.e., without an auxiliary air pump, then the cover above one of the working electrodes, e.g., above chamber 28, must be perforated to permit diffusion of sample of external air to one of the working electrodes. In this arrangement, the potential on the working electrodes is in the order of 1.5 volt versus R.H.E. (the reversible hydrogen electrode in the same electrolyte), variable on the counter electrode, and about 1.1 volt (versus R.H.E.) on the reference electrode.

FIG. 2 provides a three-electrode arrangement of sensor 50 with a single working electrode 52 and a combined counter electrode 54 and reference electrode 56. Interconnected chambers 58 and 60 with wicks 59 and 61 provide nonaqueous electrolyte to the electrodes with additional electrolyte being available through electrolyte inlets 62 and 63. Porous Teflon cover 64 is provided over the electrodes. Above the electrodes are gas chambers 66 and 68 to provide contact between the gas and electrodes. Gas inlets 70 and 72 and outlets 74 and 76 permit admittance and outflow of gas from each chamber. Cover 78 is provided to permit flow control through chambers 66 and 68.

A third sensor 80 is illustrated in FIG. 3. As illustrated, working electrode 82 and combined counter and reference electrodes 84 and 86 are vertically located on opposite sides of electrolyte chamber 88 with access to additional electrolyte being provided by inlet 90. Chambers 92 and 94 provide contact between the gas and electrodes with gas inlets 96 and 97 and gas outlets 98 and 99 providing gas flow through the chambers. Covers 100 and 101 isolate the chambers.

Figure 4:
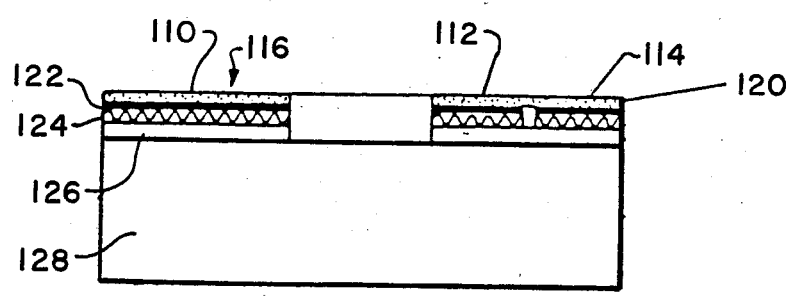
FIG. 4 is a view of a vertical cross section of the electrolyte chambers in the horizontal electrochemical sensor illustrated in FIG. 2.

As illustrated in FIG. 4, the working electrode 110 and combination of counter and reference electrodes 112 and 114 have porous Teflon membranes 116, 120 providing an interface with the gas sample. The construction of each electrode (e.g., 110) has an electrode bed 122 composed of a platinum black catalyst and about 35 wt. % of Teflon (DuPont Teflon 30) as a binder for the catalyst which is bonded to the Teflon membrane. Adjacent to the catalyst is the current collector 124 composed of a platinized Pt mesh. Next is an interface with the electrolyte composed of a first wick 126 which may be either a sintered fritted glass disk, a dual layer of a porous (30–60 micron pore size) thin (0.0025 inches) Teflon membrane (Zitex E846B-122D supplied by Chemplast, Inc., Wayne, N.J.) and Whatman filter paper #41, or a dual layer of Nafion N117 (a copolymer of tetrafluoroethylene and a perfluorosulfonic acid) membrane (treated in $H_2SO_4$) and Whatman filter paper #41. A second wick arrangement 128 is then provided composed of about 20 layers of Whatman glass fiber filter #GF/B. The above construction provides contact between the nonaqeuous electrolyte and the electrode without flooding the pores of the outer Teflon membrane.

Figure 5:
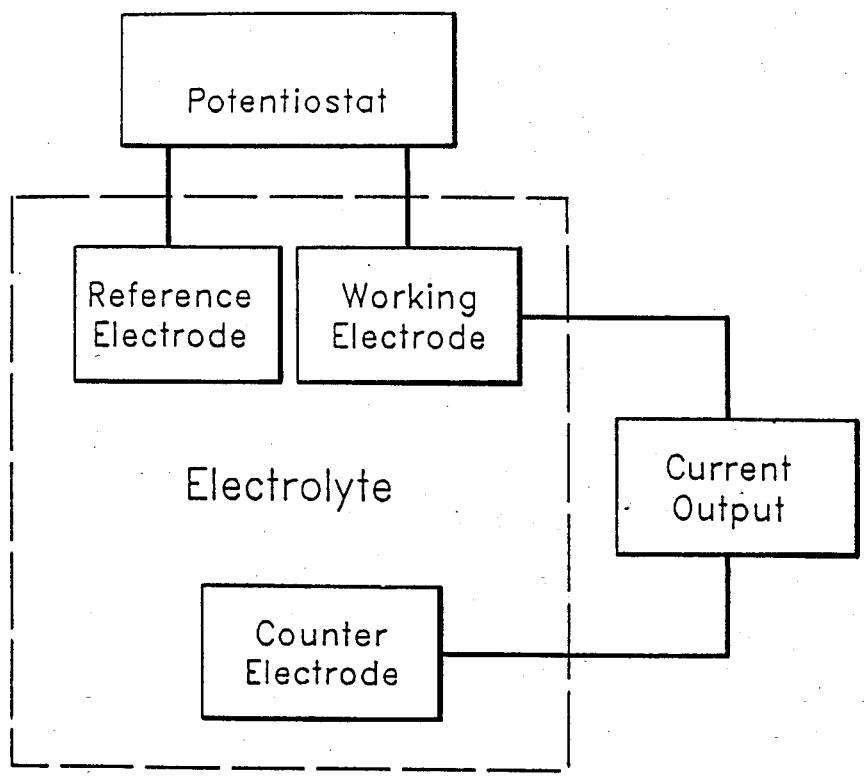
FIG. 5 is a block diagram of the electrodes and associated equipment used to provide desired voltages and to measure signal levels.

In the schematic diagram of FIG. 5, the electrical arrangement for a sensor of FIG. 2 or FIG. 3 is illustrated. A potentiostat is provided to set the voltages for the working and reference electrodes in the electrolyte. The counter electrode is externally connected to the working electrode and the current output is measured to represent the signal level from the sensor.

Figure 6:
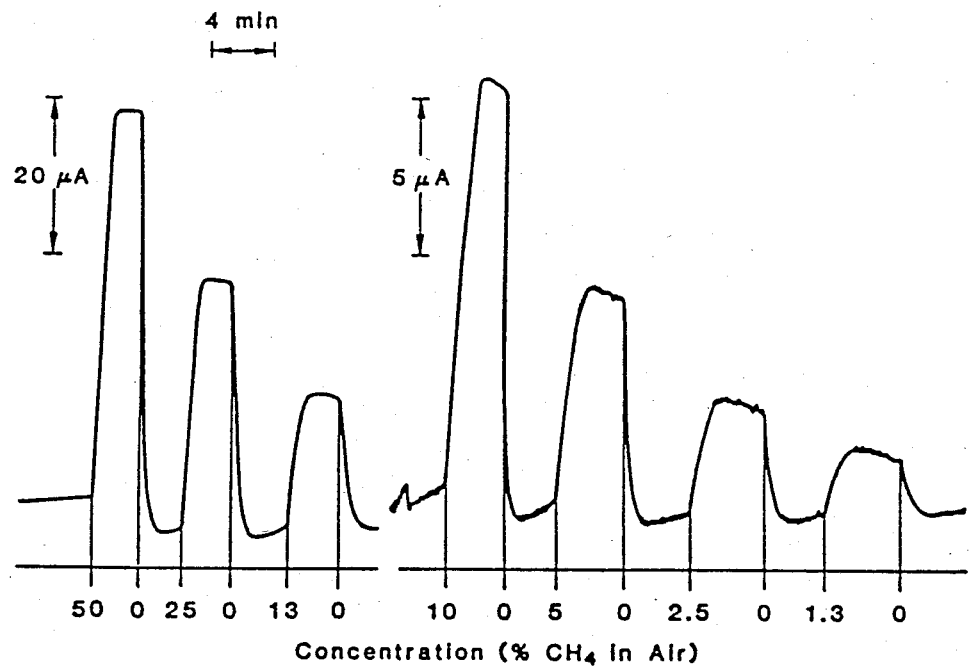
FIG. 6 is a typical chart recording of the responses of the sensor of FIG. 3 to methane in dry air.

FIG. 6 provides typical chart recordings of sensor responses to methane in dry air. These recordings were obtained by passing dry samples in air first through a "zero" filter, that removed traces of CO, $H_2$, and other impurities from the methane samples that might have given rise to spurious sensor signals, and then through the sensor of FIG. 3 at a rate of about 100 milliliters/minute. The "zero" filter—comprising a mixture of alumina pellets coated with platinum (about 1 weight-%), alumina pellets coated with potassium permanganate, and activated carbon—serves to remove CO, $H_2$, and other electrochemically reactive impurities that are usually present in commercial methane mixtures. These impurities were previously found to yield spurious responses from other electrochemical sensors that could have been mistaken for methane signals. By inserting a "zero" filter in the sample flow line, reliability of the identifications of methane as the compound responsible for the observed responses is increased. As illustrated in FIG. 6, the responses increase as the concentration is increased, with the scale of sensor response changing from 5 microamperes to 20 microamperes at the higher concentrations.

Figure 7:
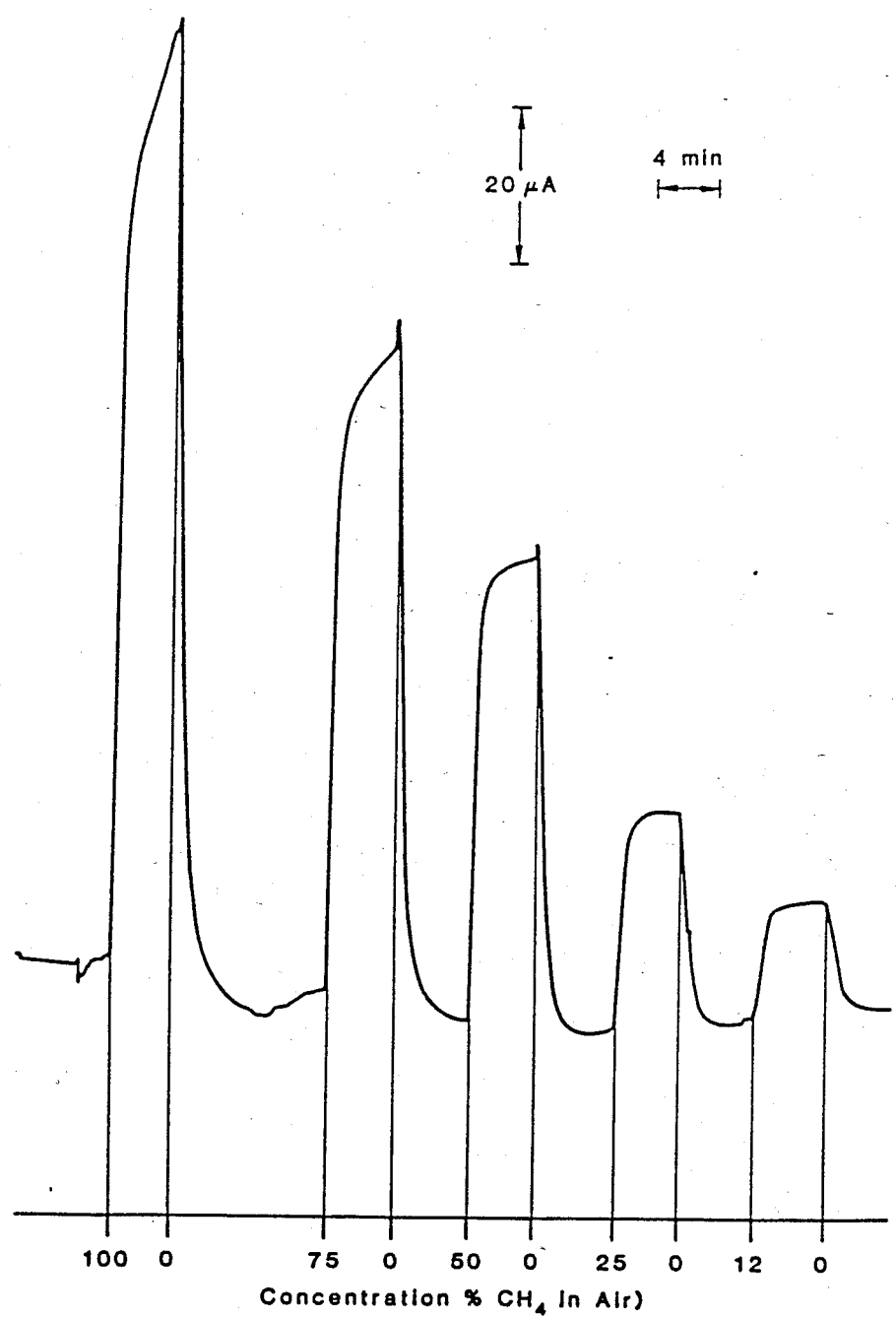
FIG. 7 is a chart recording of the responses of the sensor of FIG. 2 to methane in air at 80% relative humidity.

FIG. 7 provides a chart recording of responses of the sensor of FIG. 2 to methane in air of 80% relative humidity and room temperature. As illustrated, the response level again increases with concentration.

Figure 8:
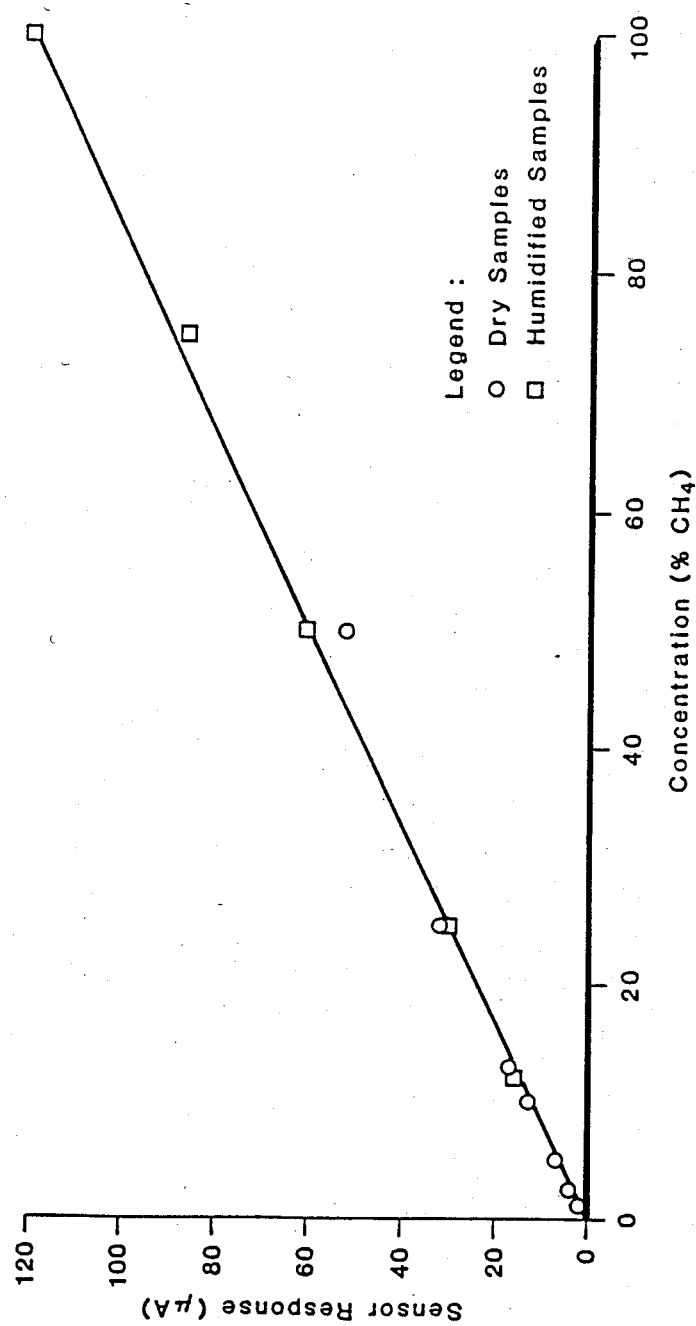
FIG. 8 is a representation of the sensor response versus methane concentration for the data of FIGS. 6 and 7.

In FIG. 8, the response of FIGS. 6 and 7 are plotted versus concentration and follow a similar linear relationship for both sensors and different conditions.

Figure 9:
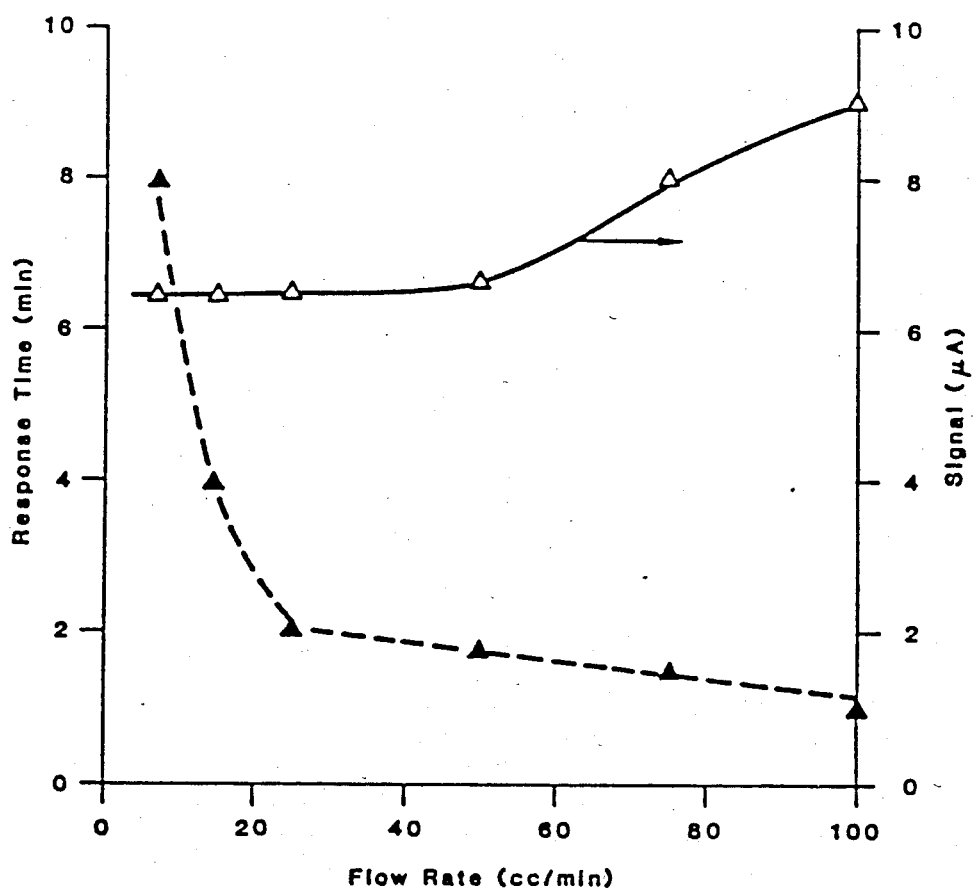
FIG. 9 is a representation of the flowrate dependence of response and response time for dry samples of 10% $CH_4$ in air.

FIG. 9 provides a representation of the flowrate dependence of the response and response time for dry samples of 10% $CH_4$ in air. As illustrated, the signal gradually decreases as the flowrate is reduced. However, below about 50 milliliters/minute, the signal is substantially constant and retains about 70% of its value at 100 milliliters/minute. This may enable the sensor to be usable without a pump in a diffusion mode. The response time decreases sharply as the flow rate increases from about 6 milliliters/minute to over 20 milliliters/minute. Above about 20 milliliters/minute, the response time decreases slowly with increasing flowrate.

One of the two working electrodes of FIG. 1, which may be denoted as the compensating electrode, is used to compensate the main working electrode for variations in background current due to changes in ambient temperature and humidity. The main working electrode is exposed to the sampled air that may contain methane, whereas the other electrodes are exposed only to methane-free air. Both the working and compensating electrodes are maintained at approximately ambient temperature and are exposed to the same source of water vapor that ensures approximately the same high relatively high humidity in gas chambers 28 and 30.

To compensate for background current variations, each of the two working electrodes is connected to a different potentiostat circuit through terminal W1 or W2 of FIG. 10. The outputs of the two potentiostat circuits are subtracted in an adder circuit, and the net background-free signal is provided by the meter circuit of FIG. 10. A background calibration circuit permits adjustments of the adder circuit in case the two working electrodes are not exactly identical. In FIG. 10 the following designations are used:

A1, A2: Active Low-Pass Filter
B1, B2: Bias Feedback Buffer
LM308: Operational Amplifier
AD532J: Integrated Circuit Multiplier
C: Counter electrode
R: Reference electrode
W: Working electrode.

The foregoing description of embodiments of the invention has been presented for purposes of illustration and description. It is not intended to be exhaustive or to limit the invention to the precise form disclosed, and obviously many modifications and variations are possible in light of the above teaching.

The embodiments of the invention in which an exclusive property or privilege is claimed are defined as follows:

1. A methane sensing instrument comprising
    an electrochemical cell including a working electrode and a second electrode, and a nonaqueous electrolyte interposed between said two electrodes and in contact with said electrodes,
    means for applying a voltage above about 1.4 volt versus R.H.E. to the working electrode, said working electrode being capable of oxidizing methane at said voltage,
    means for exposing the working electrode to a gas sample, and
    means for measuring an electrical signal in one of said electrodes, the signal being generated by a chemical reaction of any methane in said sample coming in contact with and reacting at said working electrode.

2. The instrument of claim 1, wherein said working electrode comprises platinized platinum or platinum black.

3. The instrument of claim 1 wherein the working electrode is attached to a surface membrane of gas-permeable material to permit access of the gas to the electrode.

4. The instrument of claim 3 wherein the nonaqueous electrolyte includes a nonaqueous solvent and a salt dissolved in said solvent.

5. The instrument of claim 4 wherein the means for exposing the electrode to the gas sample includes a filter means to remove any CO or $H_2$ from said sample.

6. The instrument of claim 4 wherein the working electrode includes a wick in contact with the electrolyte to maintain electrolyte in contact with the working electrode.

7. The instrument of claim 6 wherein said wick comprises sintered fritted glass or a dual layer of filter paper and either polytetrafluoroethylene or a copolymer of tetrafluoroethylene and a perfluorosulfonic acid.

8. The instrument of claim 7 wherein said wick also comprises multiple layers of glass fiber filter.

9. The instrument of claim 4 wherein said surface membrane is made of a nonporous chemically inert material that is not soluble in said nonaqueous electrolyte.

10. The instrument of claim 4 wherein said surface membrane is made of a porous material.

11. The instrument of claim 10 wherein said membrane is made of polytetrafluoroethylene.

12. The instrument of claim 4 wherein the solvent for the electrolyte is $\gamma$-butyrolactone, propylene carbonate or a mixture thereof.

13. The instrument of claim 4 wherein a second working electrode is used to compensate for variations in background current.

14. The instrument of claim 13 comprising an electrical circuit for subtracting the signals from the two working electrodes as to yield a net signal that is compensated for variations in background current.

15. The instrument of claim 4 wherein said salt is sodium or lithium perchlorate.

16. A method of determining the presence of methane in a gas comprising the steps of
providing an electrochemical cell with a working electrode and a second electrode, and a nonaqueous electrolyte interposed between said two electrodes and in contact with said electrodes,
applying an oxidizing voltage of at least about 1.4 volt versus R.H.E. to the working electrode,
exposing the working electrode to said gas so that methane in said gas reaching said working electrode is oxidized at said voltage thereby generating an electrical signal at the working electrode representative of methane in the gas, and
measuring said signal as an indication of the concentration of methane in said gas.

17. The method of claim 16 including the step of providing a gas permeable membrane adjacent the gas opposite the electrolyte.

18. The method of claim 17 including the step of feeding the gas through a filter to remove any CO or $H_2$ from the gas.

19. The method of claim 18 including the step of maintaining the electrolyte in contact with the working electrode by a wick.

* * * * *